United States Patent

Adams et al.

[11] Patent Number: 5,263,977
[45] Date of Patent: Nov. 23, 1993

[54] ELECTRODE SPACING DEVICE

[75] Inventors: Theodore P. Adams, Edina; Kenneth M. Anderson, Bloomington, both of Minn.

[73] Assignee: Angeion Corporation, Plymouth, Minn.

[21] Appl. No.: 966,870

[22] Filed: Oct. 26, 1992

[51] Int. Cl.⁵ .............................................. A61N 1/05
[52] U.S. Cl. .................................................. 607/122
[58] Field of Search ................ 128/784, 785, 786, 642

[56] References Cited

U.S. PATENT DOCUMENTS

| | | | |
|---|---|---|---|
| 4,519,404 | 5/1985 | Fleischhacker | 128/786 |
| 4,825,871 | 5/1989 | Cansell | 128/786 |
| 5,044,375 | 9/1991 | Bach, Jr. et al. | 128/786 |
| 5,090,422 | 2/1992 | Dahl et al. | 128/784 |

FOREIGN PATENT DOCUMENTS 337035  4/1988  European Pat. Off. ............ 128/786

Primary Examiner—William E. Kamm
Assistant Examiner—Scott M. Getzow
Attorney, Agent, or Firm—Anthony G. Eggink

[57] ABSTRACT

A separation device to insulate implantable elements in the right ventricle of the heart. The separation devices include peripheral structures that are constructed and arranged to mount to one of the implantable elements. Further disclosed are collapsible, compressible and resilient separation structures and those molded of biodegradable and soluble compositions.

18 Claims, 4 Drawing Sheets

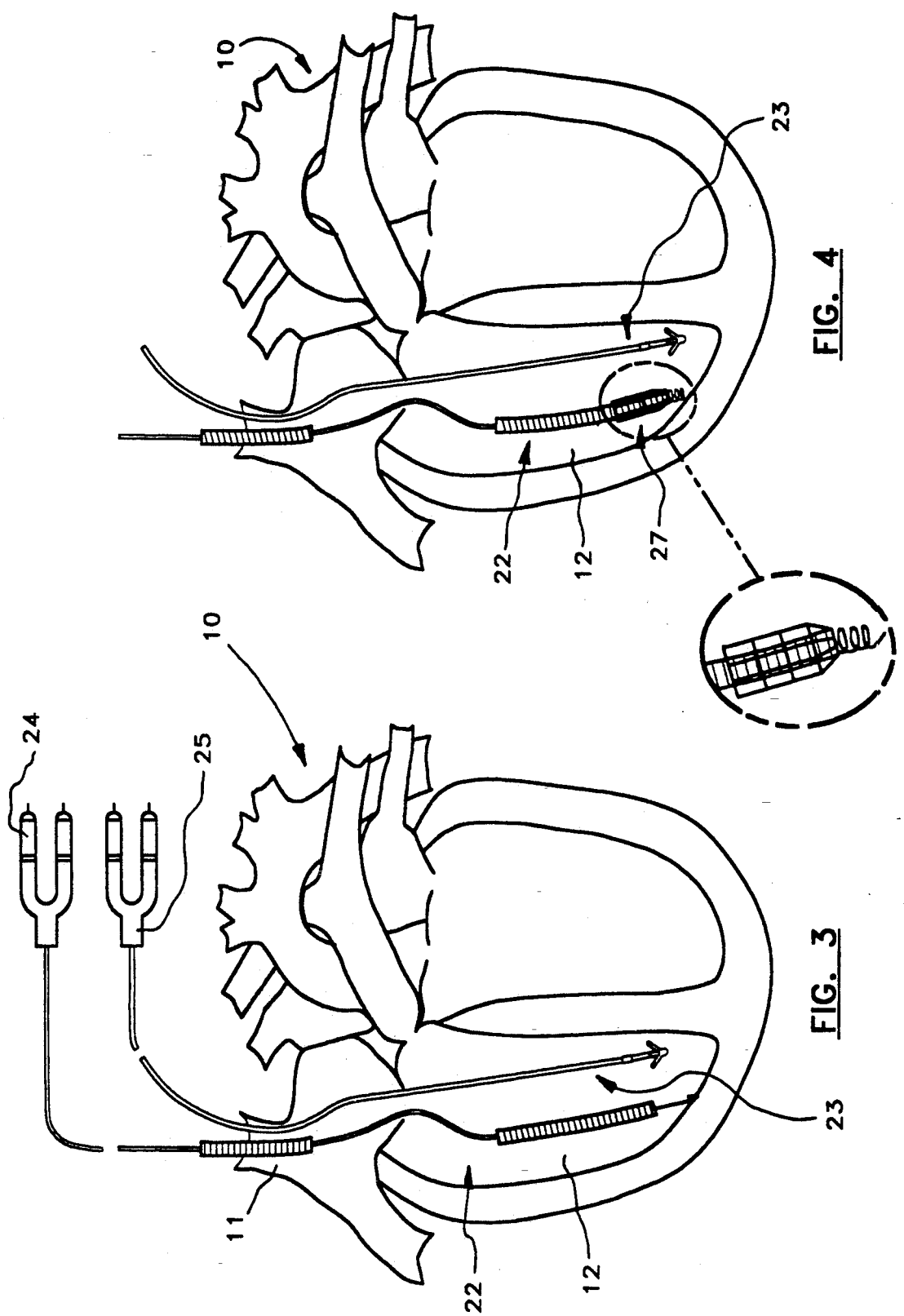

5,263,977

ELECTRODE SPACING DEVICE

BACKGROUND OF THE INVENTION

This invention relates to separation devices for implantable electrodes and, particularly, to separation devices for spacing defibrillation electrodes from pacing electrodes implanted in the right ventricle of the heart.

Various types of implantable defibrillator electrodes and associated pacing/sensing electrode elements have been proposed and utilized in implantable defibrillator systems. Each particular system and associated elements have advantages and disadvantages which effect the usefulness, reliability and efficiency of the defibrillation system.

It has been found that by building the defibrillation electrode and the pacing/sensing electrodes into distinctly different catheters offers advantages over those configurations which combine these functions in a single catheter. As will be further discussed below, it has been found preferable to utilize two separate electrode structures in the right ventricle of the heart as opposed to combining the electrodes into one unitary structure. The electrode spacing devices of the present invention are designed for use with implantable electrode and pacing/sensing electrode structures which are separately implanted in the right ventricle of the heart.

SUMMARY OF THE INVENTION

The present invention provides separation devices to maintain a minimum separation between the two implantable leads in the right ventricle of the heart. The devices comprise spacing structures which are integral with or which extend from one of the leads.

The separation devices include peripheral structures that are constructed and arranged to attach to one of the implantable elements. Further provided are collapsible and resilient separation structures suitable for transvenous implantation and those molded of biodegradable and soluble compositions.

These and other benefits of this invention will become clear from the following description by reference to the drawings.

BRIEF DESCRIPTION OF THE DRAWINGS

FIG. 3 is a sectional view showing a defibrillation electrode and a pacing electrode positioned in a side by side arrangement in the right ventricle of the heart;

FIG. 4 is a sectional view showing the electrode placement of FIG. 3 having a separation device of the present invention positioned about the defibrillation catheter electrode;

DESCRIPTION OF THE PREFERRED EMBODIMENTS

Figure 1:
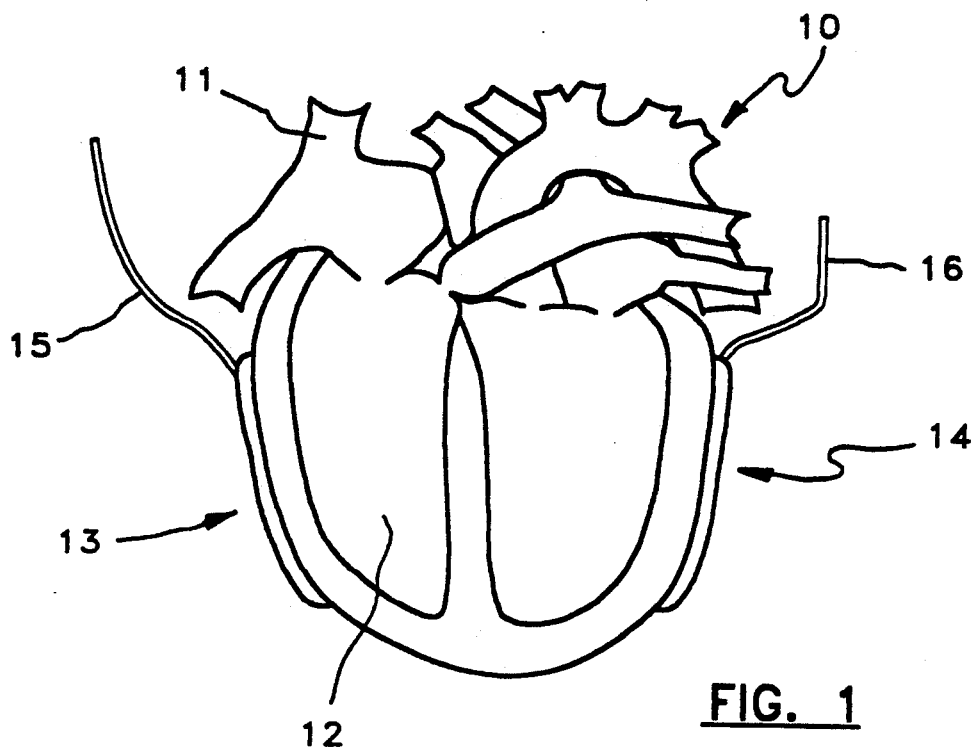
FIG. 1 is a sectional view of the heart showing epicardial patch electrodes positioned thereon.

As background information, FIG. 1 shows presently utilized implantable defibrillators which are patch type electrodes 13 and 14 that are placed on the heart's epicardium. Distinctly different pacing electrodes (not shown) are also attached to the epicardium for sensing cardiac activity. As shown, the epicardial patch electrodes 13 and 14 with leads 15 and 16, respectively, are placed outside but in contact with the heart surface 10.

Figure 2:
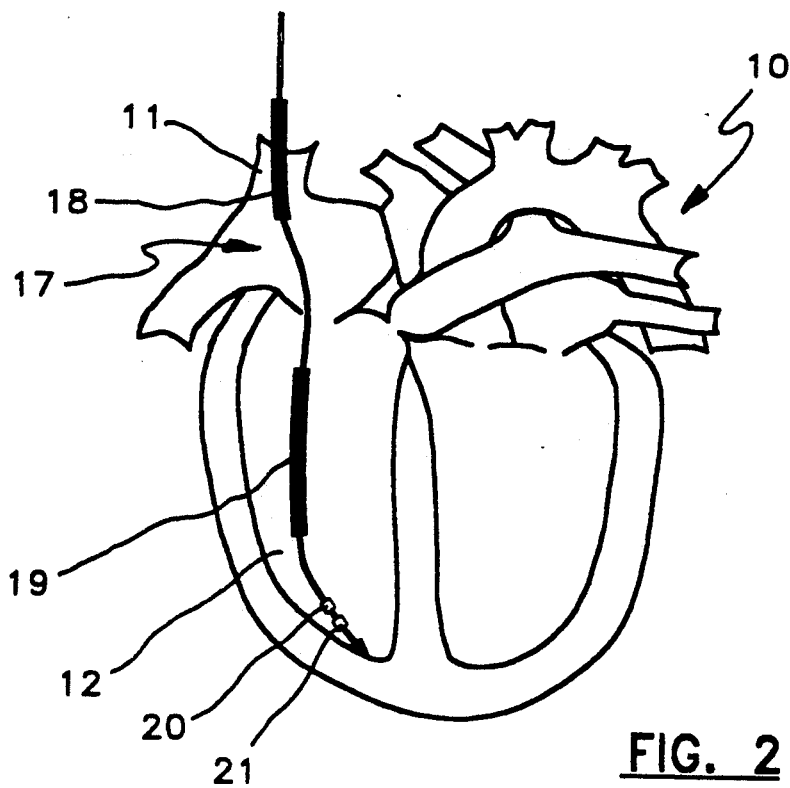
FIG. 2 is a sectional view of the heart showing a typical defibrillation electrode with a pacing electrode positioned in the right ventricle.

FIG. 2 shows an electrode configuration 17 implanted via a transvenous approach wherein a catheter having both sensing/pacing electrodes 20 and 21 and defibrillation electrodes 18 and 19 is inserted into the right ventricle of the heart. This electrode configuration is taught by Bach, U.S. Pat. No. 5,044,375. As shown, the transvenous defibrillation/pacing structure 17 is positioned in the right ventricle 12 of the heart 10 whereby the SVC electrode is located in the superior vena cava and the distal defibrillation electrode 19 and the pacing and sensing electrodes 20 and 21 are located in the right ventricle. A subcutaneous patch is sometimes used in conjunction with the transvenous electrode lead 17. This transvenous system obviates the need for a thoracotomy to implant patches on the heart and is therefore a less traumatic procedure to the patient.

As shown in FIG. 2, the currently preferred leads implanted via the transvenous approach have both the pacing/sensing electrodes 20 and 21 and the defibrillating electrodes 18 and 19 on a single catheter structure 17. Although advantages exist in combining all of these functions into one catheter structure, these devices have several disadvantages. For example, by using the distal end of the catheter for the pacing pacing/sensing electrodes, the length of the distal defibrillating electrode is shortened because of those structures. As taught in Applicant's assignee's patent disclosures, i.e., Kroll, Low Impedance Defibrillation Catheter Electrode, Ser. No. 07/915,065, Filed Jul. 16, 1992, an increased length of the defibrillating electrode will yield lower defibrillation thresholds. Furthermore, the Ideker U.S. Pat. No. 4,827,932 teaches that by implanting the defibrillating electrode closer to the heart's apex also reduces defibrillation thresholds. Thus, the presence of pacing electrodes distal to the defibrillation electrode precludes these benefits. Another unfavorable aspect of a combined pacing/defibrillation lead is that the diameter of the lead is increased over conventional pacing leads due to the necessity of carrying four conductors and providing adequate insulation between them. These structures, therefor, require larger diameter vein introducers making it difficult to enter patients with small veins and which may present a safety concern because the catheter must pass between the tight space between the clavical and ribs which rub and wear on the lead, especially large diameter leads.

In view of the above noted shortcomings, FIG. 3 shows an electrode configuration taught by Bach, U.S. Pat. No. 5,044,375, wherein a separate pacing lead 23 and a small diameter defibrillation lead 22 are both inserted side by side in the right ventricle 12. This configuration solves the threshold and size problems, but creates another. In the configuration of FIG. 3, the pacing electrodes of structure 23 can rub against the defibrillation electrode of structure 22 causing electrical artifacts on the sensing electrodes which may cause false sensing. In addition, if the two electrodes are in contact during defibrillation, the sensing electrodes are left with a large after potential (polarization voltage) which renders post shock sensing ineffectual.

Figure 5:
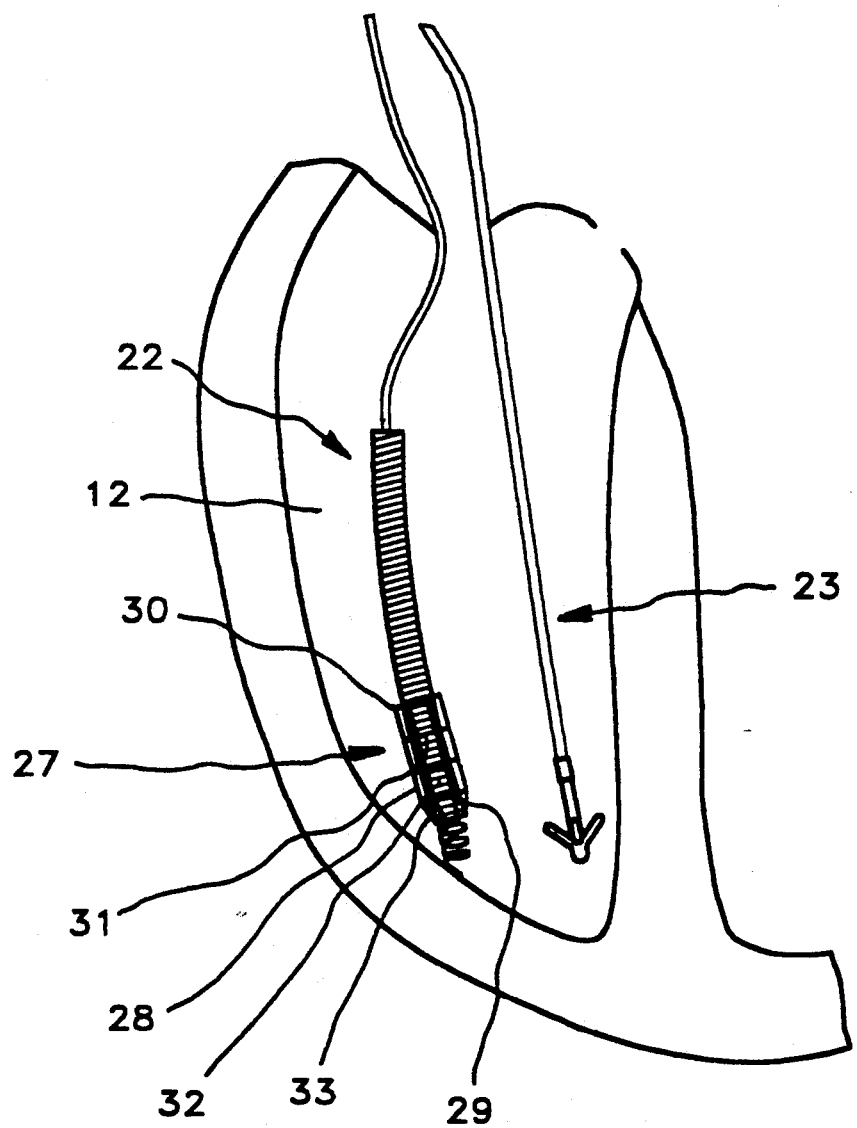
FIG. 5 is a perspective view showing the separation device of this invention positioned about a defibrillation catheter electrode which is positioned between the sensing/pacing electrode structure and the defibrillation catheter electrode.

The present invention utilizes the advantages of the above referenced two-lead system by providing protection against the possibility of the pacing electrodes touching the defibrillation electrode. As shown in FIGS. 4 and 5, a flexible cage or spacing device 27 is positioned about the distal end of the defibrillation electrode 22. The device 27 may surround either pacing/sensing electrodes on the pacing lead or, preferably, surround the lower portion of the distal defibrillation lead 22. The cage 27 can be constructed of known biocompatible lead materials, such as silicone rubber, polyurethane or the like. As shown particularly in FIG. 5, the spacing Cage 27 has a plurality of longitudinal legs 28 and 33 which are connected to leading, inner and trailing circumferential members 29, 31, 32 and 30, respectively. The leading circumferential member 29 has a diameter which permits the spacing cage 27 to be frictionally held at the distal end of the defibrillation electrode 22. Alternatively, the spacing cage 27 can be molded to the insulator portion, i.e., silicone rubber, located at the end of the lead or electrode structure 22. Thus, the spacing cage 27 embodiment, and the other embodiments described below, may be molded and subsequently positioned on the implantable lead or they may be molded directly to the lead or molded to a nonconductive portion that is an element of the lead structure. The leading legs 33 are shown to extend angularly from circumferential member 29 and connected to the inner circumferential member 32. A plurality of longitudinal legs 28 are shown connected to the circumferential member 32 and are respectively connected to and supported by circumferential members 31 and 30.

In essence, the spacing device 27 provides a cage type structure mounted at the distal end of the defibrillation electrode 22 and which provides a protective area about the electrode to ensure spacial separation from the pacing/sensing lead structure 23. Although the spacing cage embodiment 27 is shown connected or mounted to the distal end of lead 22, it may be otherwise or further supported to other portions of the lead. For example, the trailing end of the cage structure may be supported in a manner similar to that of the leading end. The spacing cage 27 provides a structure defining a plurality of open areas whereby the equidistantly spaced longitudinal legs 28 are spaced a predetermined distance to prevent the pacing lead structure 23 from penetrating and making physical contact with the defibrillation electrode portion of the lead 22.

The spacing cage device 27 is preferably constructed of a biocompatible material having flexible and resilient properties. The flexible and resilient properties of the cage device 27 allow it to be wrapped around the defibrillation electrode lead 22 during introduction through a vein introducer. Subsequent implantation, these flexible properties allow the device 27 to flex during heart contractions so as not to irritate the endocardium. The cage device 27 has sufficient stiffness to prevent the two electrode leads 22 and 23 in the right ventricle 12 from touching and to maintain separation of at least a quarter inch, for example, during the initial few days after implantation. Thereafter, the leads become encased in endothelial growth, a process termed "fibrosis". This growth will eventually cover the entire lower portions of both leads. For that reason, the cage device 27 may be constructed from a biodegradable or soluble material which will break down or dissolve as fibrosis develops. After fibrosis has occurred, the leads are permanently isolated from each other and the cage is no longer needed.

Figure 6:
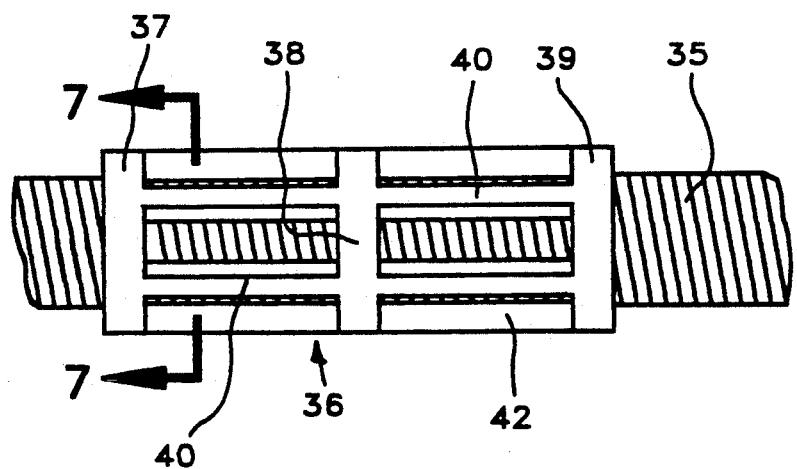
FIG. 6 is a lateral view showing another separation device embodiment of the invention positioned about a defibrillation coil electrode.
Figure 7:
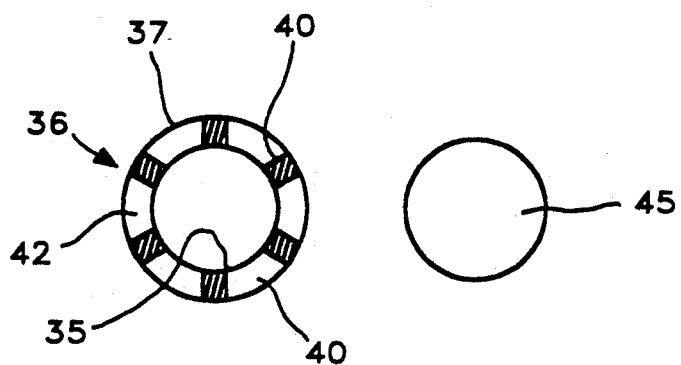
FIG. 7 is a cross-sectional view of the separation device taken along lines 7—7 of FIG. 6.

FIGS. 6 and 7 show another spacing or insulator device 36 wherein the protector device is shown positioned or molded over the defibrillation electrode coil 35 of a lead. The spacing embodiment 36 has leading, inner and trailing circumferential members 37, 38 and 39, respectively, which are interconnected by a plurality of longitudinal leg members 40. In FIG. 7, a cross-sectional view of FIG. 6, the spacing leg members 40 and circumferential bands 37, 38 and 39 are shown to extend from the electrode 35, so that the pacing/sensing lead 45 cannot touch the electrode material 35. As with the other spacing embodiments, the longitudinal spaces 42 in device 36 expose the electrode material 35 so that the electrode material is in contact with blood and/or tissue. The outwardly extending body portions, i.e., members 37, 38, 39 and 40, define spaced apertures 42 which have dimensions that prevent the lead 45 from touching the conductive portion 35 of the lead. Although the outwardly positioned body portions may be positioned or molded a few millimeters, or fractions thereof, from electrode 35, the important aspect of this invention is to maintain physical separation between implantable leads and to prevent physical touching. As described above with respect to the prior art and the spacing embodiment of FIG. 5, a greater separation distance may be desired to also minimize electrical field effects.

Figure 8:
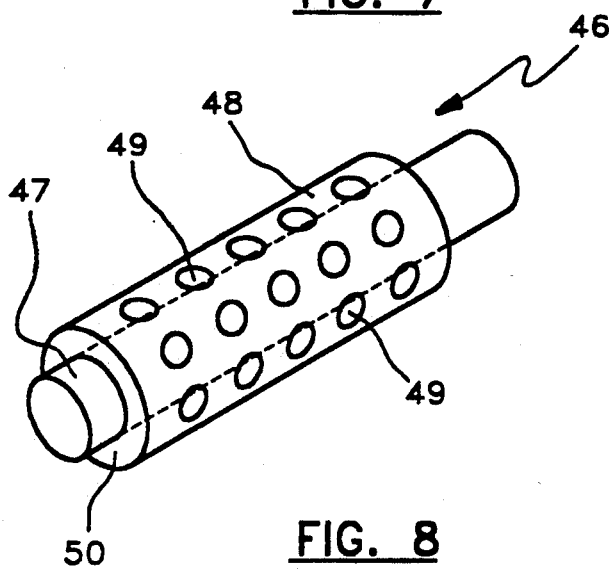
FIG. 8 is a perspective view of another spacing device embodiment of the invention.

FIG. 8 shows another spacing or insulator embodiment 46 connected to and surrounding implantable element 47. This embodiment 46 is similar to that of FIG. 6, except rather than having elongated spaces 42, a plurality of apertures 49 are utilized in body 48. The spacing device 46 has a body structure 48 constructed of a biocompatible material which may be molded about or constructed to frictionally fit around the electrode element 47. The device 46 has an elongated body 48 with a wall thickness 50 and a plurality of apertures 49. The apertures 49 may have a variety of shapes or configurations, however, the important aspect being the physical separation between the implantable elements. The respective body structures shown in FIGS. 6 and 8 may be constructed of the same materials as described above with respect to the other embodiments of this invention. The spacing assemblies 36 and 46 may be constructed of short body sections of insulation material that is positioned over the conductive coil portions 35 and 47 and which are perforated with openings 42 and 49 as large as possible but small enough to keep the sensing electrode of the pacing catheter from touching. In the configurations as shown in FIGS. 6 and 8, the defibrillation lead and protector assemblies 36 and 46 are constructed and arranged to fit through a smaller diameter introducer. And, as with the other embodiments of this invention, the spacing assemblies 36 and 46 protect the respective implanted leads from touching to prevent producing undesired mechanically generated electrical artifacts.

As many changes are possible to the embodiments of this invention utilizing the teachings thereof, the descriptions above, and the accompanying drawings should be interpreted in the illustrative and not in the limited sense.

We claim:

1. A separation device to insulate implantable elements in the ventricle of a heart comprising spacing means for connection to and extension from one said implantable element, said spacing means being a peripheral structure comprised of a biodegradable composition and having an axial bore and connecting means constructed and arranged for attachment to one said implantable element.

2. The separation device of claim 1, wherein said spacing means is comprised of a tubular member having at least one aperture and wherein said tubular member is constructed and arranged to prevent the touching of the implantable elements.

3. The separation device of claim 1, wherein said spacing means is constructed of a cage structure having connecting members with opposing ends attaching said cage structure and said implantable element.

4. The separation device of claim 1, wherein one said implantable element has a nonconductive portion and wherein said spacing means is molded to said nonconductive portion.

5. The separation device of claim 1, wherein said spacing means is a non-conductive material molded about one said element, said non-conductive material having a plurality of apertures therethrough.

6. The separation device of claim 1, wherein said spacing means is collapsible for transvenous implantation.

7. A compressible electrode spacing device for separating an implantable defibrillation electrode having a conductive portion from a sensing electrode in the ventricle of a heart, said spacing device comprising a generally cylindrical, compressible and resilient body structure constructed of a biodegradable material and having a generally constant and predetermined thickness for surrounding the conductive portion of said implantable defibrillation electrode and means for connecting said device to said implantable defibrillation electrode.

8. The electrode spacing device of claim 7, wherein said body structure is constructed and arranged of a tubular body having an axial bore for positioning about said defibrillation electrode, said body structure having a wall and at least one aperture through said wall.

9. The electrode spacing device of claim 7, wherein said body structure has at least one connecting member for receiving said defibrillation electrode.

10. The electrode spacing device of claim 9, wherein said body structure further has a plurality of longitudinally extending leg members attached to said at least one connecting member.

11. The electrode spacing device of claim 7, wherein said compressible and resilient body structure is comprised of a silicone rubber or polyurethane material.

12. The electrode spacing device of claim 7, wherein said compressible and resilient body structure is comprised of a material soluble in blood.

13. The electrode spacing device of claim 7, wherein said predetermined thickness of said cylindrical body is at least one quarter inch.

14. The electrode spacing device of claim 7, wherein said generally cylindrical body structure has a plurality of apertures therethrough to expose said defibrillation electrode, said apertures having predetermined dimensions and being constructed and arranged to prevent said spacing electrode from passing through said apertures.

15. A separation device to insulate implantable elements having a conductive portion in the right ventricle of a heart comprising an insulative, generally cylindrical body structure for mounting to one said implantable element, said cylindrical body structure being constructed of a material soluble in blood and having a predetermined diameter and further having means to mount said device to said implantable element, said device having at least one aperture therethrough to expose the conductive portion of said implantable element.

16. The separation device of claim 15, wherein said body structure is an elongated structure having an axial bore and wherein said body structure is molded of a non-conductive, biocompatible plastic composition.

17. The separation device of claim 16, wherein said elongated body structure has a plurality of apertures therethrough and wherein said plastic composition is a compressible and resilient composition.

18. A separation device to insulate implantable elements in the ventricle of a heart comprising spacing means for connection to and extension from one said implantable element, said spacing means being comprised of a non-conductive material soluble in blood, said spacing means further comprising a peripheral structure having at least one aperture therethrough and having connecting means constructed and arranged for attachment to one said implantable element.

* * * * *